United States Patent
Walter et al.

(10) Patent No.: US 8,660,665 B2
(45) Date of Patent: *Feb. 25, 2014

(54) ELECTRODE ARRANGEMENTS FOR TISSUE STIMULATION AND METHODS OF USE AND MANUFACTURE

(75) Inventors: Jeryle L. Walter, Valencia, CA (US); Greg Terterian, Granada Hills, CA (US); Matthew Flowers, Valencia, CA (US); Robert R. Tong, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/620,196

(22) Filed: Sep. 14, 2012

(65) Prior Publication Data

US 2013/0008026 A1    Jan. 10, 2013

Related U.S. Application Data

(63) Continuation of application No. 11/609,586, filed on Dec. 12, 2006, now Pat. No. 8,290,599.

(51) Int. Cl.
*A61N 1/05* (2006.01)

(52) U.S. Cl.
USPC ............................................ 607/117; 607/116

(58) Field of Classification Search
USPC ........ 600/372, 374; 607/2, 54, 115–119, 129, 607/141–142, 152
See application file for complete search history.

(56) References Cited

U.S. PATENT DOCUMENTS

| 3,718,142 | A | 2/1973 | Mulier |
| 3,941,136 | A | 3/1976 | Bucalo |
| 4,033,357 | A | 7/1977 | Helland et al. |
| 4,135,518 | A | 1/1979 | Dutcher |
| 4,301,815 | A | 11/1981 | Doring |
| 4,542,753 | A | 9/1985 | Brenman et al. |
| 4,585,005 | A | 4/1986 | Lue et al. |
| 4,702,254 | A | 10/1987 | Zabara |
| 4,722,353 | A | 2/1988 | Sluetz |

(Continued)

FOREIGN PATENT DOCUMENTS

| WO | 9837926 A1 | 9/1998 |
| WO | 9843701 A1 | 10/1998 |
| WO | 9843700 A9 | 7/1999 |
| WO | 0117315 A1 | 3/2001 |

OTHER PUBLICATIONS

Official Communication, U.S. Appl. No. 11/609,586, mailed Jan. 23, 2009.

(Continued)

*Primary Examiner* — Carl H Layno
*Assistant Examiner* — Jennifer Ghand
(74) *Attorney, Agent, or Firm* — Frommer Lawrence & Haug LLP; Bruce E. Black (57) ABSTRACT

A lead has a paddle body with a non-conductive material and multiple electrodes disposed within the non-conductive material. At least one of the electrodes includes one or more anchoring arrangement, such as opening(s) through the electrode through which the non-conductive material can pass; anchors that extend away from the electrode and into the non-conductive material of the paddle body; or flow-through anchors attached to the electrode with an opening through which the non-conductive material may pass.

18 Claims, 5 Drawing Sheets

(56) References Cited

U.S. PATENT DOCUMENTS

| | | |
|---|---|---|
| 4,796,643 A | 1/1989 | Nakazawa et al. |
| 4,867,164 A | 9/1989 | Zabara |
| 4,957,118 A | 9/1990 | Erlebacher |
| 5,025,807 A | 6/1991 | Zabara |
| 5,193,539 A | 3/1993 | Schulman et al. |
| 5,193,540 A | 3/1993 | Schulman et al. |
| 5,312,439 A | 5/1994 | Loeb |
| 5,314,457 A | 5/1994 | Jeutter et al. |
| 5,376,108 A | 12/1994 | Collins et al. |
| 5,433,735 A | 7/1995 | Zanakis et al. |
| 5,439,938 A | 8/1995 | Snyder et al. |
| 5,454,840 A | 10/1995 | Krakovsky et al. |
| 5,571,118 A | 11/1996 | Boutos |
| 5,741,319 A | 4/1998 | Woloszko et al. |
| 5,775,331 A | 7/1998 | Raymond et al. |
| 5,938,584 A | 8/1999 | Ardito et al. |
| 6,038,484 A | 3/2000 | Kuzma |
| 6,051,017 A | 4/2000 | Loeb et al. |
| 6,058,332 A | 5/2000 | Dahl |
| 6,181,969 B1 | 1/2001 | Gord |
| 6,188,932 B1 | 2/2001 | Lindegren |
| 6,516,227 B1 | 2/2003 | Meadows et al. |
| 6,604,283 B1 | 8/2003 | Kuzma |
| 6,609,029 B1 | 8/2003 | Mann et al. |
| 6,609,032 B1 | 8/2003 | Woods et al. |
| 6,650,943 B1 | 11/2003 | Whitehurst et al. |
| 6,735,474 B1 | 5/2004 | Loeb et al. |
| 6,741,892 B1 | 5/2004 | Meadows et al. |
| 6,757,970 B1 | 7/2004 | Kuzma et al. |
| 6,788,975 B1 | 9/2004 | Whitehurst et al. |
| 7,244,150 B1 | 7/2007 | Brase et al. |
| 7,596,414 B2 | 9/2009 | Whitehurst et al. |
| 7,610,103 B2 | 10/2009 | Whitehurst et al. |
| 7,672,734 B2 | 3/2010 | Anderson et al. |
| 7,706,892 B2 | 4/2010 | Colvin et al. |
| 7,761,165 B1 | 7/2010 | He et al. |
| 7,840,279 B2 | 11/2010 | He |
| 7,953,498 B1 | 5/2011 | Carbunaru et al. |
| 7,974,706 B2 | 7/2011 | Moffitt et al. |
| 8,175,710 B2 | 5/2012 | He |
| 2002/0128700 A1 | 9/2002 | Cross |
| 2003/0204228 A1 | 10/2003 | Cross et al. |
| 2004/0059392 A1 | 3/2004 | Parramon et al. |
| 2004/0122500 A1 | 6/2004 | Rouns |
| 2005/0004638 A1* | 1/2005 | Cross, Jr. .................. 607/117 |
| 2005/0085884 A1 | 4/2005 | O'Brien et al. |
| 2005/0154435 A1 | 7/2005 | Stern et al. |
| 2007/0150036 A1 | 6/2007 | Anderson |
| 2008/0046049 A1 | 2/2008 | Skubitz et al. |
| 2008/0140168 A1 | 6/2008 | Walter et al. |

OTHER PUBLICATIONS

Official Communication, U.S. Appl. No. 11/609,586, mailed Aug. 6, 2009.

Official Communication, U.S. Appl. No. 11/609,586, mailed Dec. 8, 2009.

Official Communication, U.S. Appl. No. 11/609,586, mailed Jun. 8, 2010.

Official Communication, U.S. Appl. No. 11/609,586, mailed Mar. 1, 2012.

* cited by examiner

ELECTRODE ARRANGEMENTS FOR TISSUE STIMULATION AND METHODS OF USE AND MANUFACTURE

CROSS-REFERENCE TO RELATED APPLICATIONS

This patent is a continuation of U.S. patent application Ser. No. 11/609,586 filed on Dec. 12, 2006, now U.S. Pat. No. 8,290,599 issued Oct. 16, 2012, which is incorporated herein by reference.

FIELD

The present invention is directed to the area of devices and methods for stimulation of tissue using an array of electrodes, as well as methods of making and using the devices. In addition, the present invention is directed to the area of devices and methods for stimulation of tissue using electrodes with an anchoring mechanism to retain the electrodes within a paddle body, as well as methods of making and using the devices.

BACKGROUND

Stimulators have been developed to provide therapy for a variety of disorders, as well as for other treatments. For example, stimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

As one example, spinal cord stimulation is a well accepted clinical method for reducing pain in certain populations of patients. Stimulators have been developed to provide therapy for a variety of treatments. For example, stimulators can be used to stimulate nerves, such as the spinal cord, muscles, or other tissue. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

BRIEF SUMMARY

One embodiment is a lead having a paddle body with a non-conductive material and multiple electrodes disposed within the non-conductive material. At least one of the electrodes includes a top portion, a bottom portion, and a sidewall portion extending from the top portion to the bottom portion. At least one of the electrodes defines at least one opening through which the non-conductive material extends.

Another embodiment is a lead having a paddle body with a non-conductive material and multiple electrodes disposed within the non-conductive material. At least one of the electrodes includes one or more anchors that extend away from the electrode and into the non-conductive material of the paddle body.

Yet another embodiment is a stimulation system that includes any of the leads described above and a control module coupleable to the lead for providing electrical signals to the electrodes for stimulating tissue.

A further embodiment is a method of making a lead by providing a plurality of electrodes where at least one of the electrodes includes a top portion, a bottom portion, and a sidewall portion extending from the top portion to the bottom portion. At least one of the electrodes defines at least one opening. The plurality of electrodes is disposed in a non-conductive material so that the non-conductive material passes through the at least one opening.

Yet another embodiment is a method of making a lead by providing multiple electrodes where at least one of the electrodes has one or more anchors that extend away from the electrode. The electrodes are disposed in a non-conductive material so that the one or more anchors extend into the non-conductive material.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to devices and methods for stimulation of tissue using an array of electrodes, as well as methods of making and using the devices. In addition, the present invention is directed to devices and methods for stimulation of tissue using electrodes with an anchoring mechanism to retain the electrodes within a paddle body, as well as methods of making and using the devices.

Figure 1:
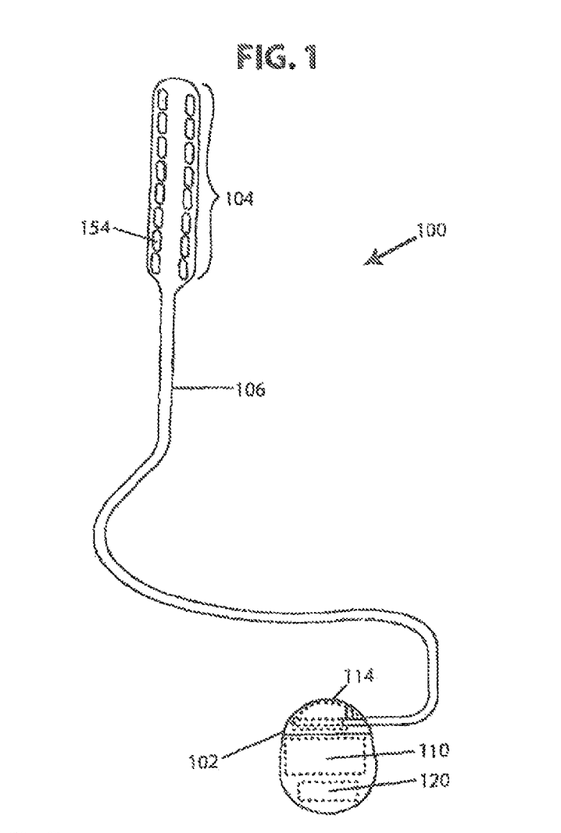
FIG. 1 is a schematic illustration of one embodiment of a stimulation system, according to the invention.

FIG. 1 illustrates schematically one embodiment of a stimulation system 100. The stimulation system includes a control module (e.g., a stimulator or pulse generator) 102, a paddle body 104, and at least one lead body 106 coupling the control module to the paddle body. The paddle body 104 and the lead body 106 form a lead. The paddle body 104 typically includes an array of electrodes 154. It will be understood that the system for stimulation can include more, fewer, or different components and can have a variety of different configurations including those configurations disclosed in the stimulation system references cited herein. Examples of stimulation systems with electrode leads are found in, for example, U.S. Pat. Nos. 6,181,969; 6,516,227; 6,609,029; 6,609,032; 6,741,892; 7,244,150; 7,672,734; 7,761,165;

7,974,706; and 8,175,710; and U.S. Patent Application Publication No. 2007/0150036, all of which are incorporated by reference. The stimulation system or components of the stimulation system, including one or more of the lead body 106, the paddle body 104 and the control module 102, are typically implanted into the body. The stimulation system can be used for a variety of applications including, but not limited to, brain stimulation, neural stimulation, spinal cord stimulation, and the like.

Figure 2:
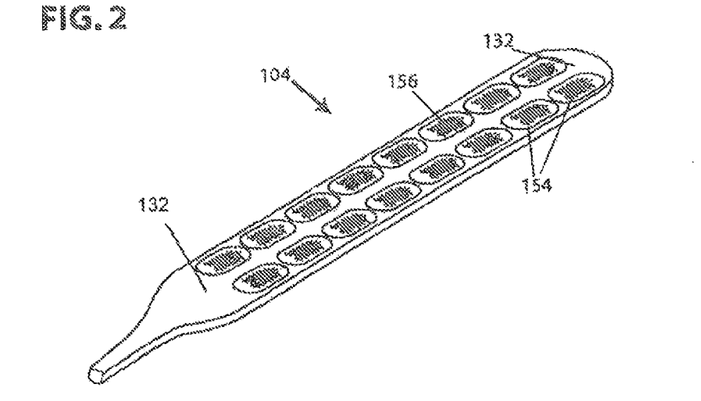
FIG. 2 is a schematic perspective top view of one embodiment of a paddle body, according to the invention.

FIG. 2 illustrates a schematic top view of one embodiment of the paddle body 104 which includes an array of electrodes 154 disposed in a non-conductive material 132. The electrodes 154 can be made using any conductive material. Examples of suitable materials include metals, alloys, conductive polymers, conductive carbon, and the like, as well as combinations thereof. The number of electrodes 154 in the array of electrodes 154 may vary. For example, there can be two, four, six, eight, ten, twelve, fourteen, sixteen, or more electrodes 154. As will be recognized, other numbers of electrodes 154 may also be used.

A variety of different arrangements of the electrode(s) 154 can be used. For example, the electrodes 154 may be arranged in an array in two or more parallel columns, as illustrated schematically in FIGS. 1 and 2. The columns of electrodes can be aligned or staggered from one another, or in any other desired column or row arrangement. The electrodes may also be arranged, for example, in a single column, or "in line," along the longitudinal axis of a small diameter lead body. In other embodiments, the electrodes may be placed circularly or elliptically or in any other suitable arrangement including any combination of arrangements described herein. The arrangement of electrodes may be symmetrical or asymmetrical.

The non-conductive material 132 of the paddle body 104 can be made of any non-conductive, biocompatible material including, for example, silicone, polyurethane, polyetheretherketone (PEEK), epoxy, and the like or combinations thereof. The non-conductive material 132 may be formed in the desired shape by any process including, for example, molding (including injection molding), casting, and the like. Preferably, the non-conductive material does not cover the top surface 156 (or at least a substantial portion of the top surface 156) of the electrodes 154.

In one embodiment, the non-conductive material 132 is molded or otherwise formed around the electrodes 154. Examples of methods for forming the paddle body in this manner are described in U.S. Patent Application Publication No. 2007/0150036, incorporated herein by reference. For example, the non-conductive material 132 can be molded around the electrodes in one or more steps. As one example, the electrodes 154 can be positioned within a mold and the non-conductive material can be molded around the electrodes leaving both the top and bottom surfaces of the electrodes exposed. Conductors (described below) can be attached to the bottom surface of the electrodes and then additional non-conductive material can be molded over the bottom surface of the electrodes.

In at least some embodiments, the non-conductive material flows around the electrodes during a molding process. The non-conductive material then becomes a solid mass to set the paddle shape. This process of conversion to a solid mass may be a result of cooling the non-conductive material, for example; if the flowing material is a thermoplastic polymer. In some embodiments, the non-conductive material that flows during the molding process is initially a monomeric material or an uncrosslinked polymeric material. The non-conductive material may then be formed into a solid mass by, for example, polymerizing the monomeric material or crosslinking the polymeric material (or any combination thereof.)

Figure 6:
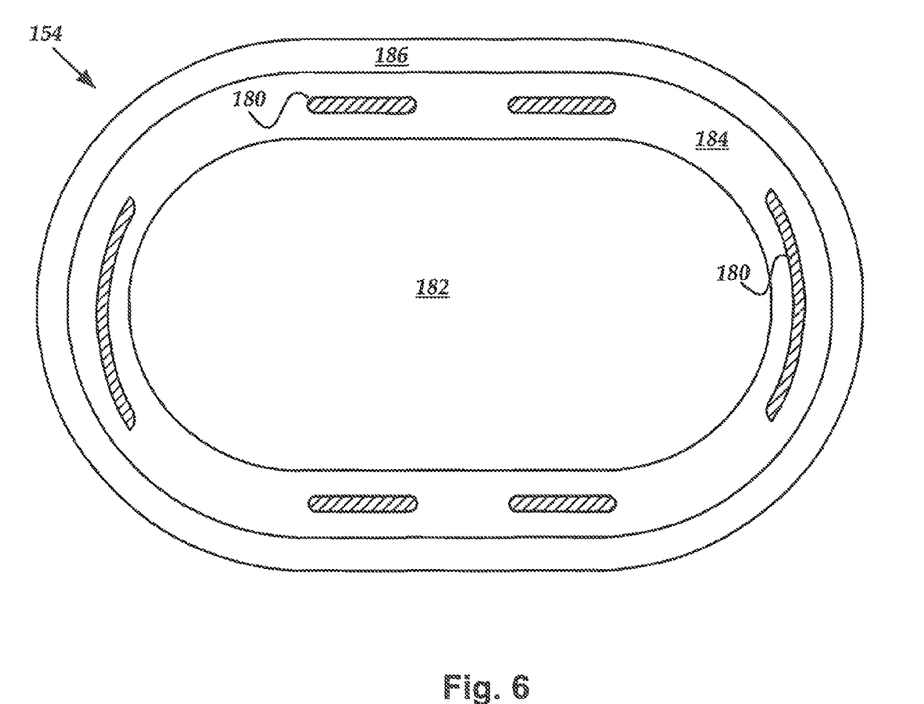
FIG. 6 is a schematic bottom view of a third embodiment of an electrode, according to the invention.
Figure 7:
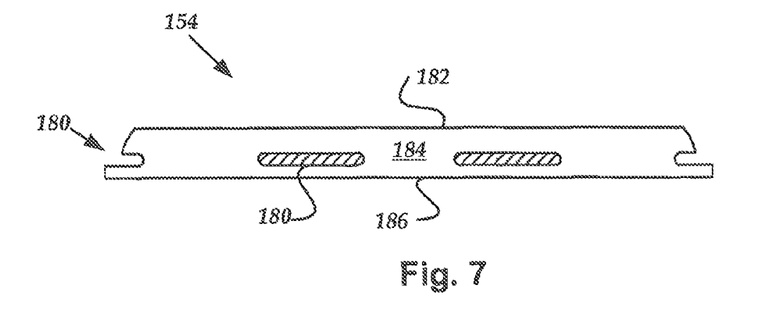
FIG. 7 is a schematic side view of the electrode of FIG. 6.

Because the electrodes 154 and the non-conductive material 132 may be made of dissimilar materials (e.g. metal and plastic) there may be some tendency for the materials to separate during or after manufacture. FIGS. 6 and 7 schematically illustrate a bottom view and a side view, respectively, of one embodiment of an electrode 154 with one or more openings 180. During manufacture, and in some instances even afterwards, the non-conductive material molded around the sides and bottom of the electrode can extend through the openings 180. This can provide stability for the electrode 154 within the paddle body 104.

The electrode 154 of the illustrated embodiment has a pot-like or bowl-like shape (see, e.g., FIG. 4) with a top portion 182 (the bottom surface of which is seen in FIG. 6) with a sidewall portion 184 extending to a bottom portion 186. This bottom portion 186 may be flanged, as illustrated in FIG. 6, to provide for stability within the non-conductive material.

Figure 8:
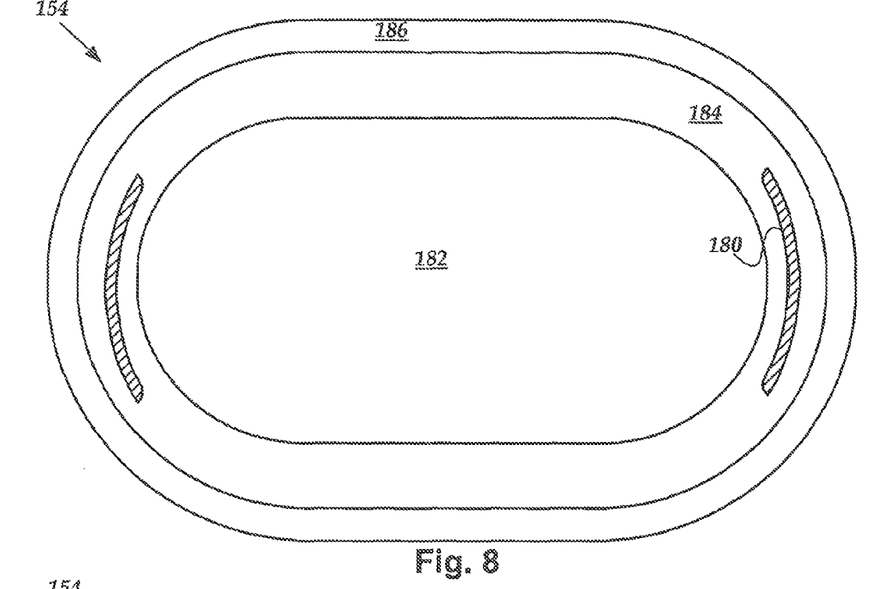
FIG. 8 is a schematic bottom view of a fourth embodiment of an electrode, according to the invention.
Figure 9:
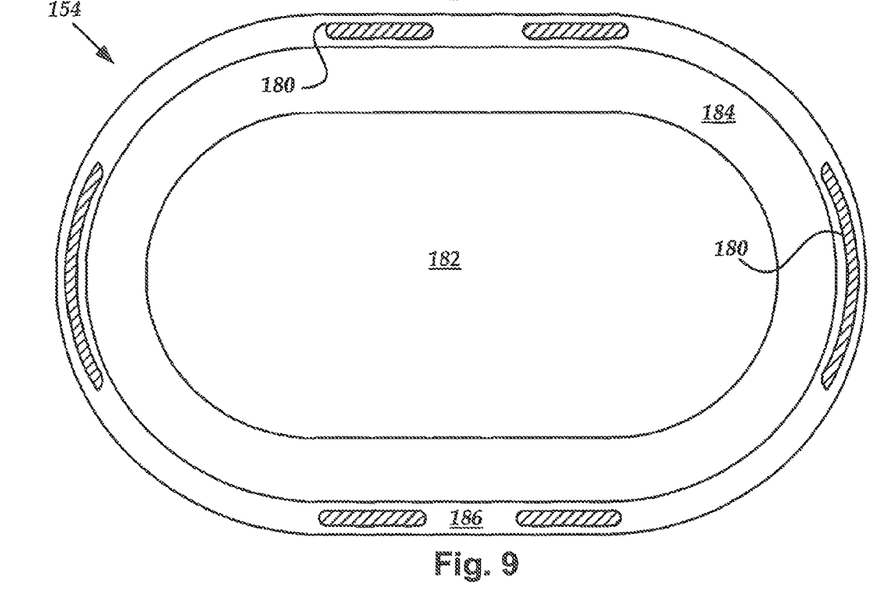
FIG. 9 is a schematic bottom view of a fifth embodiment of an electrode, according to the invention.

The openings 180 are typically formed in the sidewall portion 184 or bottom portion 186 (see FIG. 9) of the electrode 154. The electrode can include one or more openings 180. If the electrode 154 includes multiple openings 180, these openings can be spaced in any arrangement including symmetrical and non-symmetrical arrangements. FIG. 6 illustrates openings at the ends of the electrode, as well as along the longitudinal sides of the electrode. FIG. 8 illustrates another embodiment with openings 180 only at ends of the electrode. FIG. 9 illustrates yet another embodiment with openings positioned on the flange forming the bottom portion 186 of the electrode 154. It will be recognized that some embodiments may have openings in both the sidewall portion 184 and bottom portion 186.

The openings 180 can have any shape. In the illustrated embodiment, the openings have a slot shape. The openings 180 are typically sufficiently wide and long to permit the non-conductive material to flow, or otherwise pass, through the openings. In one embodiment, the openings have a width in the range of 0.001, to 0.01, inches (e.g., 0.025, to 0.25, mm) and a length in the range of 0.01, to 0.1, inches (e.g., 0.25, to 2.5, mm). In one embodiment, the non-conductive material flows through the openings and then cools, or is polymerized or cross-linked, to form a solid mass that passes through the openings and facilitates stability of the electrode 154 in the paddle body 104.

Figure 3:
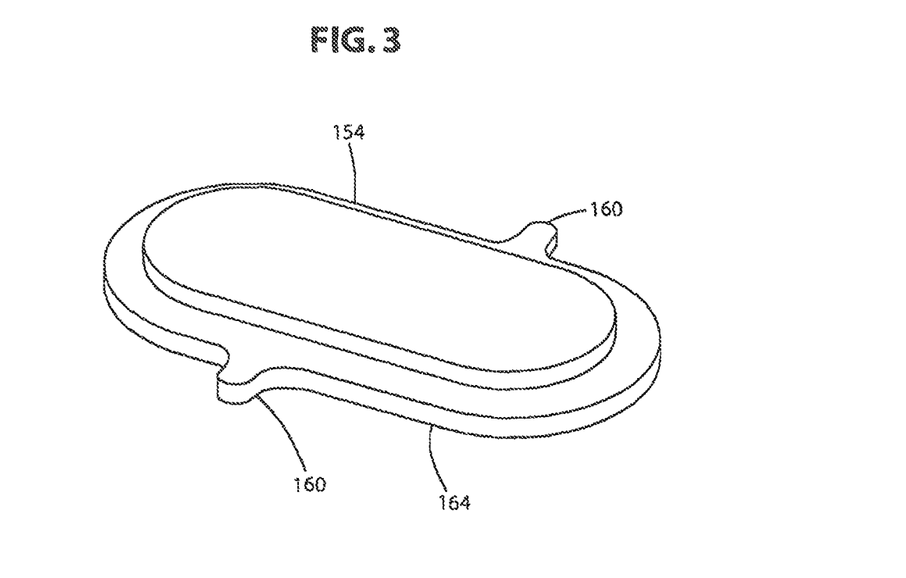
FIG. 3 is a schematic perspective top view of one embodiment of an electrode, according to the invention.
Figure 4:
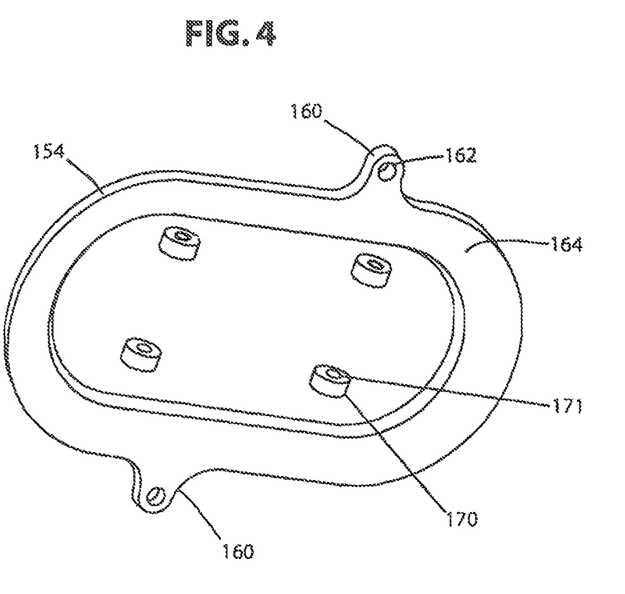
FIG. 4 is a schematic perspective bottom view of another embodiment of an electrode, according to the invention.

There are other anchoring arrangements. FIGS. 3 and 4 schematically illustrate top and bottom views, respectively, of one embodiment of an electrode 154 with one or more anchors 160. These anchors 160 extend into the non-conductive material 132 to facilitate retention of the electrode 154 within the non-conductive material 132. Generally, the top and bottom surfaces of the anchors are covered by the non-conductive material 132 when the electrodes is in place within the completed paddle body 104. Accordingly, the position of the anchors on the electrode 154 is selected with the understanding that the top surface 156 of the electrode is typically exposed. In the illustrated embodiments of FIGS. 3 and 4, the anchors 160 extend from, or near, a bottom surface 164 of the electrode 154. In an alternative embodiment, the anchors 160 can extend inwardly (for example, inward from the bottom surface of the electrode) beneath the top surface of the electrode. There should be space between the top surface and the anchor for the non-conductive material.

When more than one anchor 160 is used, the anchors can be disposed in any manner around the electrode 154. In one embodiment, at least two anchors 160 are disposed on opposite sides of the electrode 154 as illustrated, for example, in FIGS. 3 and 4. There may be one or more anchors on each opposite side. In other embodiments, anchors can extend from three or four sides of the electrode. Optionally, the anchors may be offset laterally from each other, as illustrated, for example in FIGS. 3 and 4, to further facilitate retention.

The size and shape of the anchors 160, the length that the anchors extend from the electrode 154, and the number and placement of anchors 160 can vary and may be selected to provide a desired amount of stability of the electrode within the paddle body 104. Length of the anchors may be restricted by the separation distance between adjacent electrodes to avoid contact. By offsetting the anchors laterally (as illustrated, for example, in FIGS. 3 and 4) the anchors of adjacent electrodes may be offset from each other to avoid contact while allowing closer placement.

Optionally, the anchor 160 may include one or more openings 162 that extends through the anchor. The non-conductive material 132 may pass through the opening(s) 162 to further facilitate retention of the electrode 154 within the non-conductive material 132. Moreover, if the non-conductive material 132 is molded around the electrode 154, a portion of the non-conductive material may pass through the opening(s) 162 during the molding process to provide further stability for the electrode within the non-conductive material.

Yet another anchoring arrangement is illustrated in FIG. 4 as one or more attached flow-through anchors 170. In the illustrated embodiment, the flow-through anchors are attached to a surface of the electrode (for example, the bottom surface of the electrode as illustrated in FIG. 4) and include an opening 171 through which the non-conductive material may pass during the molding process. When set, the non-conductive material that extends through the opening can provide mechanical stability to retain the electrode within the non-conductive material. The flow-through anchors may have a cylindrical shape, as illustrated in FIG. 4, or any other suitable shape with an opening through which the non-conductive material may flow. The flow-through anchors can be made of any material and attached to the electrode in any manner. In one embodiment, the flow-through anchors are made of metal and attached by welding or soldering the anchors to the electrode.

Turning again to FIG. 1, a conductor (not shown) is attached to each of the electrodes 154 and extends along the lead body 106 to the control module 102 to conduct electrical pulses from the control module to the electrode. Preferably, the conductor is attached to the back side of the electrode 154, which is the side of the electrode 154 opposite the side that will be exposed to the body tissue.

The conductors can be made of any conductive material. Examples of suitable material for conductors include metals, alloys, conductive polymers, conductive carbon, and the like, as well as combinations thereof in one embodiment, the conductors are insulated by an insulating material except where the conductor makes contact with the electrode 154. The insulating material may be any material that is a poor conductor of an electrical signal, including, for example, Teflon™, nylon, Mylar, other non-conductive polymers, and composite materials. The conductors may be attached to the electrodes by any method including, for example, resistance welding, laser welding, conductive epoxy, and the like. Preferably, the conductors are attached to the electrodes 154 by a method that results in a durable attachment of the conductors to the electrodes 154 under expected usage conditions.

The lead body 106 is typically made of a non-conductive material such as, for example, silicone, polyurethane, polyetheretherketone (PEEK), epoxy, and the like. Optionally, the lead body may include one or more lumens through which the conductors pass or through which a drug or other medication can pass to the site of stimulation near the electrodes 154. The lead body 106 also may include a connector (not shown) for attachment to the control module 102 with contacts to connect the conductors to corresponding contacts of the control module.

The control module 102 typically includes a housing 114 with an electronic subassembly 110 and, in at least some embodiments, a power source 120 disposed within a chamber in the housing. Preferably, the housing is resistant to moisture penetration into the chamber containing the electronic subassembly and power source. In some embodiments, water may diffuse through the housing. Preferably, the diffused water is relatively pure, without substantial ionic content, as deionized water is relatively non-conductive. The housing 114 may be made of any biocompatible material including, for example, glass, ceramics, metals, and polymers, as well as combinations thereof. Preferably, the material of the plastic housing is a hydrophobic polymer material. The housing 114 may include additives such as, for example, fillers, plasticizers, antioxidants, colorants, and the like. The thickness of the walls of the housing may also impact the moisture permeability of the housing. A minimum thickness needed to achieve a particular degree of resistance to moisture transport will often depend on the material selected for the housing, as well as any additives.

Optionally, the housing 114 can be covered, in full or in part, with a coating. The coating can be provided to improve or alter one or more properties of the housing 114 including, for example, biocompatibility, hydrophobicity, moisture permeability, leaching of material into or out of the housing, and the like. In one embodiment, a coating can be applied which contains a compound, such as, for example, a drug, prodrug, hormone, or other bioactive molecule, that can be released over time when the control module is implanted. In another embodiment, the housing itself may include such a compound to be released over time after implantation.

Figure 5:
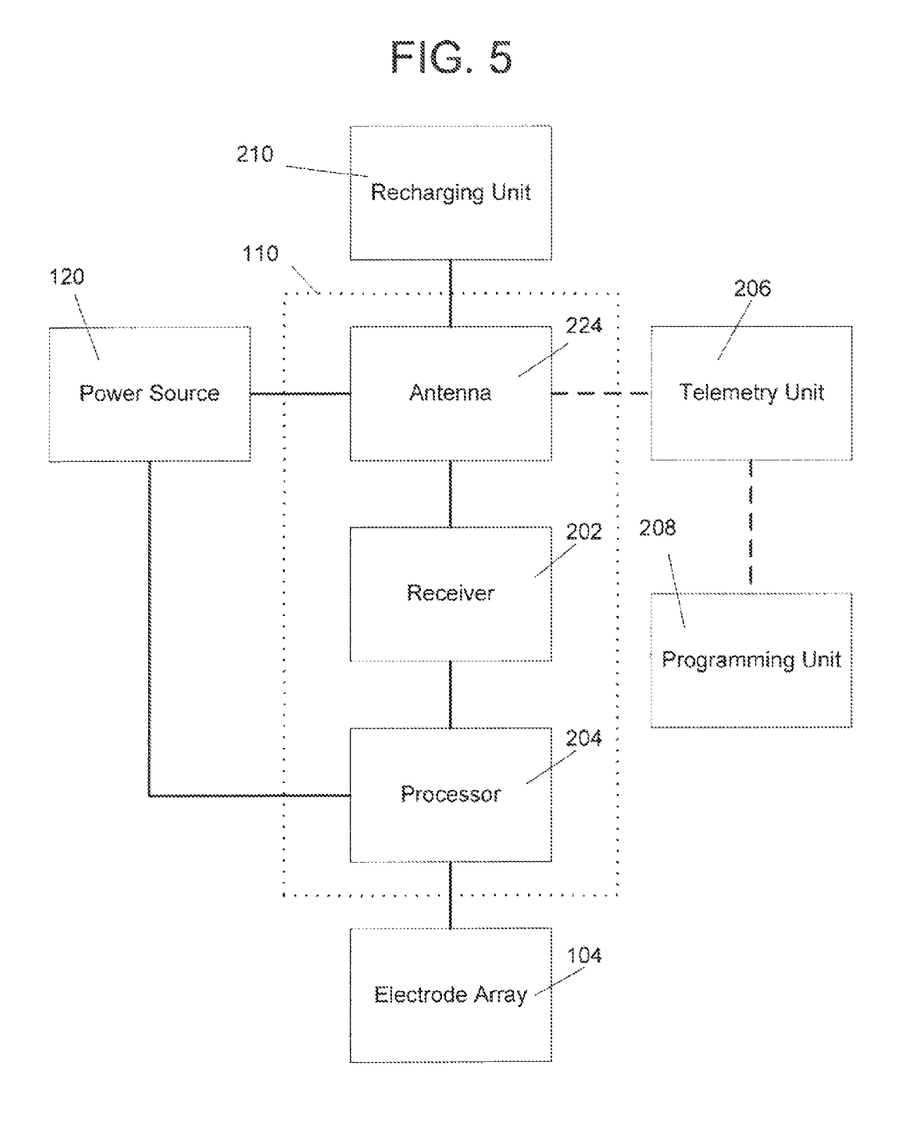
FIG. 5 is a schematic block diagram of one embodiment of a stimulation system, according to the invention.

FIG. 5 is a schematic overview of one embodiment of components of a system for stimulation, including an electronic subassembly 110 (which may or may not include the power source 120), according to the invention. It will be understood that the system for stimulation and the electronic subassembly 110 can include more, fewer, or different components and can have a variety of different configurations including those configurations disclosed in the stimulation system references cited herein. Some or all of the components of the system for stimulation can be positioned on one or more circuit boards or similar carriers within a housing of a control module, if desired.

Any power source 120 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No, 2004/0059392, incorporated herein by reference.

As another alternative, power can be supplied by an external power source through inductive coupling via the optional antenna 224 or a secondary antenna. The external power source can be in a device that is mounted on the skin of the user or in a unit that is provided near the control module user on a permanent or periodic basis.

If the power source 120 is a rechargeable battery, the battery may be recharged using the optional antenna 224, if desired. Power can be provided to the battery 120 for recharging by inductively coupling the battery through the antenna to a recharging unit 210 external to the user. Examples of such arrangements can be found in the stimulation system references identified above.

In one embodiment, electrical current is emitted by the electrodes 154 to stimulate motor nerve fibers, muscle fibers, or other body tissues. The electronic subassembly 110 provides the electronics used to operate the stimulation system and generate the electrical pulses at the electrodes 154 to produce stimulation of the body tissues.

In the illustrated embodiment, a processor 204 is generally included in the electronic subassembly 110 to control the timing and electrical characteristics of the stimulation system. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments with electrodes disposed on two or more sides of the housing, the processor may be used to identify which electrodes provide the most useful stimulation of the desired tissue. This process may be performed using an external programming unit, as described below, that is in communication with the processor 204.

Any processor can be used. For example, the processor can be as simple as an electronic device that produces pulses at a regular interval or the processor can be complex and capable of receiving and interpreting instructions from an external programming unit 208 that allow modification of pulse characteristics. In the illustrated embodiment, the processor 204 is coupled to a receiver 202 which, in turn, is coupled to the optional antenna 224. This allows the processor to receive instructions from an external source to direct the pulse characteristics and the selection of electrodes, if desired.

In one embodiment, the antenna 224 is capable of receiving signals (e.g. RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulation system. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 224 and receiver 202 can be used to modify or otherwise direct the operation of the stimulation system. For example, the signals may be used to modify the pulses of the stimulation system such as modifying one or more of pulse duration, pulse frequency, pulse waveform, and pulse strength. The signals may also direct the stimulation system to cease operation or to start operation or to start charging the battery. In other embodiments, the electronic subassembly 110 does not include an antenna 224 or receiver 202 and the processor operates as programmed.

Optionally, the stimulation system may include a transmitter (not shown) coupled to the processor and antenna for transmitting signals back to the telemetry unit 206 or another unit capable of receiving the signals. For example, the stimulation system may transmit signals indicating whether the stimulation system is operating properly or not or indicating when the battery needs to be charged. The processor may also be capable of transmitting information about the pulse characteristics so that a user or clinician can determine or verify the characteristics.

The optional antenna 224 can have any form. In one embodiment, the antenna comprises a coiled wire that is wrapped at least partially around the electronic subassembly within or on the housing.

Any method of manufacture of the components of the system for stimulation can be used.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making a lead, comprising:
   providing a plurality of electrodes including a first electrode, wherein the first electrode comprises a top portion, a bottom portion, and a sidewall portion extending from the top portion to the bottom portion, the first electrode defining at least one opening, wherein the sidewall portion of the first electrode defines the at least one opening; and
   in a single molding operation, molding a homogeneous non-conductive material around the plurality of electrodes to form a portion of a paddle body with the non-conductive material holding the plurality of electrodes together, wherein a portion of the non-conductive material flows into and through the at least one opening of the first electrode, a portion of the non-conductive material defines at least a top surface of the paddle body, and a portion of the non-conductive material extends from the top surface of the paddle body through the at least one opening of the first electrode.

2. The method of claim 1, wherein molding a homogenous non-conductive material around the plurality of electrodes comprises flowing the non-conductive material through the at least one opening of the first electrode and then forming a solid mass with the non-conductive material.

3. The method of claim 2, wherein forming a solid mass with the non-conductive material comprises polymerizing or cross-linking the non-conductive material.

4. The method of claim 1, wherein each of the plurality of electrodes comprises a top portion, a bottom portion, and a sidewall portion extending from the top portion to the bottom portion and each of the plurality of electrodes defines at least one opening, wherein molding a homogenous non-conductive material around the plurality of electrodes comprises flowing the non-conductive material through the at least one opening of each of the plurality of electrodes.

5. The method of claim 1, further comprising attaching a conductor to each of the plurality of electrodes.

6. The method of claim 1, wherein molding the non-conductive material comprises molding the non-conductive material leaving exposed at least a portion of a top surface of each of the plurality of electrodes.

7. The method of claim 1, wherein at least one of the plurality of electrodes further comprises a first elongated side, a second elongated side opposite the first elongated side, shorter third and fourth rounded sides that extend between the first and second elongated sides, and at least one anchor that extends into the non-conductive material of the paddle body and away from the first elongated side or the second elongated side of the electrode in a direction that is parallel to a top surface of the at least one of the plurality of electrodes.

8. The method of claim 7, wherein the at least one anchor has a lateral width that is substantially less than a lateral width of the first or second elongated side from which it extends.

9. The method of claim 1, wherein the at least one opening has a slot shape.

10. A method of making a lead, comprising:
providing a plurality of electrodes including a first electrode, wherein the first electrode comprises a top surface, a first elongated side, a second elongated side opposite the first elongated side, shorter third and fourth rounded sides that extend between the first and second elongated sides, wherein the first electrode comprises a top portion, a bottom portion opposite the top portion, and a sidewall portion extending from the top portion to the bottom portion, and wherein the top portion defines a bottom surface of the top portion that is surrounded by the sidewall portion, wherein one or more flow-through anchors are disposed on the bottom surface of the top portion of the first electrode and at least one anchor that extends away from the first elongated side or the second elongated side of the first electrode in a direction that is parallel to the top surface of the first electrode, wherein the at least one anchor has a lateral width that is substantially less than a lateral width of the first or second elongated side from which it extends; and
molding a homogeneous non-conductive material around the plurality of electrodes to form a paddle body with a portion of the non-conductive material surrounding the at least one anchor.

11. The method of claim 10, wherein the at least one anchor comprises a first anchor disposed on and extending away from the first elongated side and a second anchor disposed on and extending away from the second elongated side.

12. The method of claim 11, wherein the first anchor and the second anchor are laterally offset from each other.

13. The method of claim 10, wherein the first electrode further comprises a top portion, a bottom portion opposite the top portion, and a sidewall portion extending from the top portion to the bottom portion, wherein the at least one anchor extends from, or near, the bottom portion of the first electrode.

14. The method of claim 10, wherein each of the plurality of electrodes comprises a top surface, a first elongated side, a second elongated side opposite the first elongated side, shorter third and fourth rounded sides that extend between the first and second elongated sides, and at least one anchor that extends away from the first elongated side or the second elongated side in a direction that is parallel to the top surface of the electrode from which it extends, wherein the at least one anchor has a lateral width that is substantially less than a lateral width of the first or second elongated side from which it extends.

15. The method of claim 14, wherein, for each of the plurality of electrodes, the at least one anchor comprises a first anchor disposed on and extending away from the first elongated side and a second anchor disposed on and extending away from the second elongated side.

16. The method of claim 15, wherein the first anchor and the second anchor are laterally offset from each other.

17. The method of claim 10, wherein each of the at least one anchor comprises an opening through the anchor.

18. The method of claim 17, wherein molding a homogeneous non-conductive material comprises flowing the non-conductive material through the opening of the at least one anchor.

* * * * *